United States Patent

Shimokawatoko et al.

[11] Patent Number: 5,844,124
[45] Date of Patent: Dec. 1, 1998

[54] METHOD AND APPARATUS FOR MEASURING ODORANT CONCENTRATION AND ODERANT ADDING SYSTEM

[75] Inventors: Takayuki Shimokawatoko; Koichi Sumida; Hirofumi Ueda, all of Osaka, Japan

[73] Assignee: Osaka Gas Co., Ltd., Osaka, Japan

[21] Appl. No.: 728,846

[22] Filed: Oct. 10, 1996

[51] Int. Cl.[6] .................................................. G01N 21/23
[52] U.S. Cl. ........................................... 73/23.34; 250/373
[58] Field of Search ................................ 73/23.2, 23.21, 73/23.34; 250/373

[56] References Cited

U.S. PATENT DOCUMENTS

| | | | |
|---|---|---|---|
| 3,694,086 | 9/1972 | May | 250/373 |
| 3,826,920 | 7/1974 | Woodroffe et al. | 250/373 |
| 3,935,463 | 1/1976 | Jacobsen | 250/373 |
| 5,604,298 | 2/1997 | Dosoretz et al. | 73/23.2 |
| 5,621,213 | 4/1997 | Barshad | 250/373 |

FOREIGN PATENT DOCUMENTS

| | | | |
|---|---|---|---|
| 0591758 | 4/1994 | European Pat. Off. | |
| 226966 | 9/1985 | Germany | 250/373 |
| 8-285766 | 11/1996 | Japan | 73/23.34 |
| 1558594 | 1/1980 | United Kingdom. | |
| 2178841 | 2/1987 | United Kingdom | 250/373 |

OTHER PUBLICATIONS

EPO; Patent Abstracts of Japan; Publ No. JP60031056; Publ Date Feb. 16, 1985; Appln No. JP 830139340; Appln Date Aug. 1, 1983; Patentee Tokyo Gas KK; Inventor O Koukichi et al; Method for Measuring Concentration of Odorant THT Ingas.

Abstract (Basic) : DE 42 32 371 A; Abstract (Equivalent) : De 42 32 371 C.

Primary Examiner—Hezron E. Williams
Assistant Examiner—Daniel S. Larkin
Attorney, Agent, or Firm—Felfe & Lynch

[57] ABSTRACT

A method, an apparatus, and an integrated system using the apparatus for measuring a concentration of odorant in odorized gas which is produced by adding the odorant to un-odorized gas comprised mainly of hydrocarbon gas. In a detection absorbance measuring step, there is obtaining detection odorized gas absorbance which is absorbance of the odorized gas relative to a detecting ultraviolet light having high absorbability to the odorant and low absorbability to the un-odorized gas. In a subsequent concentration deriving step, the odorant concentration in the odorized gas is derived from the detection odorized gas absorbance.

14 Claims, 9 Drawing Sheets operation analyzing device absorption spectrum of odorized gas added with DMS
(DMS 45.8 ppm)
measurement pressure 1.1 kgf / cm² (absolute)

absorption spectrum of odorized gas added with TBM
(TBM 44.4 ppm)
measurement pressure 1.1 kgf / cm² (absolute)

absorption spectrum of odorized gas added with THT
(THT 52.3 ppm)
measurement pressure 1.1 kgf / cm² (absolute)

absorption spectrum of un-odorized 13A gas
measurement pressure  1.1 kgf / cm² (absolute)

METHOD AND APPARATUS FOR MEASURING ODORANT CONCENTRATION AND ODERANT ADDING SYSTEM

BACKGROUND OF THE INVENTION

1. Field of the Invention

Odorant comprised of an organic sulfur compound as dimethylsufide ("DMS" hereinafter), tertiary butylmercaptan ("TBM" hereinafter), tetrahydrothiophene ("THT" hereinafter), isopropylmercaptan ("IPM" hereinafter), normalpropylnercaptan ("NPM" hereinafter), ethylpropylmercaptan ("EM" hereinafter) and diethylsulfide ("DES" hereinafter) is added to. The present invention relates to the art of measuring concentration of such odorant whose component is known in advance, in a continuous and realtime manner.

2. Description of the Related Art

According to the convention, to measure odorant concentration, sample gas is obtained, under a pressure-adjusted state into a near-atmospheric pressure from the high pressure, from a delivery pipe (a high pressure gas delivery pipe under 4 to 100 kgf/cm2 approximately) and then the measurement is effected by using a gas chromatograph device with an FPD (flame photometric detector) which is installed at an analyzing room located away from the sampling site.

The above-described conventional method has the following drawback. For the measurement, low-pressure sample gas under a near-atmospheric pressure is needed. Further, as the concentration measurement is effected by means of a gas chromatograph by separating the un-odorized gas (e.g. 13A which is one type of city gas) and the odorant component from each other. This measurement operation is time-consuming.

Accordingly, it is impossible, for instance, to quantitatively monitor the odorant concentration in the continuous and realtime manner at a certain site of a high-pressure delivery pipe. Hence, it was impossible to grasp or record accurately a time variation of the odorant concentration. Of course, the conventional method did not allow control of the odorant concentration on a realtime basis.

Therefore, a primary object of the present invention is to provide a method and apparatus for measuring the odorant concentration which are capable of solving the above-described drawback of the convention. A further object of the invention is to provide an odorant adding system which allows continuous and realtime control of odorant concentration.

SUMMARY OF THE INVENTION

For fulfilling the above-noted objects, the present invention provides a method of measuring a concentration of odorant in odorized gas which is produced by adding the odorant to the un-odorized gas which is comprised mainly of hydrocarbon gas, the method comprises:

a detection absorbance measuring step for obtaining detection odorized gas absorbance which is absorbance of the odorized gas relative to detecting ultraviolet light having a wavelength that has a high absorbability to the odorant and low absorbability to the un-odorized gas; and a concentration deriving step for deriving the odorant concentration in the odorized gas by using the detection odorized gas absorbance.

In the above method, the so-called ultraviolet light absorption method is utilized in the measurement of odorant concentration. In this respect, for measuring odorant concentration of the odorized gas produced by adding the above-described odorant to the un-odorized gas comprised mainly of hydrocarbon, there are some ultraviolet light wavelengths which have low absorbability relative to the un-odorized gas and high absorbability relative to the odorant. Ultraviolet light wavelengths having such properties are employed for the measurement, and in the detection absorbance measuring step, absorbance of the odorized gas for this ultraviolet light is obtained.

This absorbance is related (specifically, almost proportional) to the concentration of the odorant present in the odorized gas. Therefore, in the subsequent concentration deriving step, the concentration of odorant can be derived from the detection odorized gas absorbance.

Next, a specific example will be described in which DMS is added to city gas.

FIG. 3 graphically illustrates the absorbances of odorized gas produced by adding 45.8 ppm of DMS (odorant) to 13A city gas (un-odorized gas) for a variety of wavelengths. In this graph, the solid line represents the absorbance distribution for the various wavelengths.

On the other hand, FIG. 6 graphically illustrates the absorbance of the un-odorized 13A city gas for the same wavelengths. By comparing FIGS. 3 and 6 to each other, it may be seen that, for instance, that ultraviolet light having a wavelength ranging between 190 nm and 210 nm has high absorbability relative to the odorant and low absorbability relative to the un-odorized gas. Here, preferably, i.e. in a preferred embodiment to be described later, the 'high' absorbability refers to a corresponding absorbance of 0.004 or more, while the 'low' absorbability refers to a corresponding absorbance not greater than 0.004.

Further, FIG. 7 illustrates the relationship between the odorant concentration and the absorbabilities of ultraviolet light having some specific wavelengths. Namely, in this example, the ultraviolet light has wavelengths of 196 nm, 204 nm, and 209 nm, respectively.

As may be apparent from FIG. 7, there exists a substantially linear function between the odorant concentration and the absorbance. Hence, by obtaining the absorbance of the detecting ultraviolet light wavelengths, the odorant concentration may be derived from this absorbance.

Accordingly, by using the odorant concentration measuring method described above, the odorant concentration may be measured in a realtime manner even within a delivery pipe in which the gas is present under a high pressure. Further, since the method of the invention is based on measurement of the ultraviolet light absorption by the gas, the odorant concentration measurement may be done in a speedy, accurate, and continuous manner, whereby the odorant concentration may be controlled with greater ease.

In employing the above-described method, it sometimes happens that the absorption of the ultraviolet light by the un-odorized gas may remain as a noise. To solve this problem, the invention provides a further method further comprising a first correction un-odorized gas absorbance which is the absorbance of the un-odorized gas relative to the detection ultraviolet light;

wherein, an odorant-concentration corresponding absorbance is obtained from the detection odorized gas absorbance with respect to the first correction un-odorized gas absorbance; and in the concentration deriving step, the odorant concentration is derived from the odorant-concentration corresponding absorbance.

When the above method is employed, for instance, the correction of the detection odorized gas absorbance is effected by using the first correction un-odorized gas absorbance as the zero point of reference, so that the absorbance may be obtained based on the data relating solely to the odorant. As a result, the odorant concentration measurement may be effected with greater accuracy.

In the case of the above-described further method, the absorbance needs to be obtained for both the odorized gas and the un-odorized gas, relative to the detecting ultraviolet light. For this reason, this method requires two lines for sampling the respective gases, whereby the entire apparatus tends to be complicated.

Then, for avoiding such disadvantage, the invention provides a still further method in which the absorbance measurement is effected only for the odorized gas by using another ultraviolet wavelength different from that of the detecting ultraviolet light wavelength.

Namely, this method further comprise:

a second correction absorbance measuring step for obtaining a second correction odorized gas absorbance which is absorbance of the odorized gas for a correcting ultraviolet light of a wavelength having lower absorbability relative to the odorant and the hydrocarbon gas than the detecting ultraviolet wavelength;

wherein, an odorant-concentration corresponding absorbance is obtained from the detection odorized gas absorbance with respect to the second correction odorized gas absorbance; and in the concentration deriving step, the odorant concentration is derived from the odorant-concentration corresponding absorbance.

In the case of this further method, the odorant-concentration corresponding absorbance is obtained from the detection odorized gas absorbance with respect to the second correction odorized gas absorbance; and in the subsequent concentration deriving step, the odorant concentration is derived from this odorant-concentration corresponding absorbance.

In this method, for the odorized gas, there are applied two types of ultraviolet light having differing absorbability properties relative to the odorant and the hydrocarbon gas. More particularly, the detecting ultraviolet light is used as the ultraviolet wavelength for determining the odorant concentration; whereas, the correcting ultraviolet light is used as the reference ultraviolet light (e.g. for a zero-point adjustment reference). Then, the absorbances of only the odorized gas for these ultraviolet light are obtained. So that, the detection odorized gas absorbance is corrected or adjusted with reference to the second correction odorized gas absorbance and the absorbance attributable solely to the presence (concentration) of the odorant (i.e. the odorant-concentration corresponding absorbance) is derived therefrom, whereby the odorant concentration is obtained.

With the above method, the measurement can more accurately show the odorant concentration with the simple operation of obtaining the absorbances of only the odorized gas for the ultraviolet lights having differing wavelengths.

In actuality, more than two kinds of odorants are sometimes added to the un-odorized gas. In such case, individual measurement of the respective concentrations of the different odorants is desirable and important for control of odorant concentration. To cope with such a situation, the present invention then provides a still further method, in which a plurality of kinds of odorants are added to the un-odorized gas, the method comprising the steps of:

selecting in advance, as wavelengths of the detection ultraviolet light, a plurality of wavelengths having high and differing absorbabilities relative to the odorants and low absorbability relative to the un-odorized gas;

individually obtaining detection odorized gas absorbances of the odorized gas for a number of the detection ultraviolet light wavelengths greater than the number of kinds of odorants; and deriving individual concentrations of the plural kinds of odorants from the individually obtained detection odorized gas absorbances of the odorized gas.

With the above method, the concentrations of the plurality of odorants are individually measured. Therefore, absorbances of the odorized gas are obtained for the respective ultraviolet light wavelengths which are provided in a number greater than the number of kinds of odorants. On the other hand, the absorbance for each single kind of odorant of a predetermined concentration for each of these ultraviolet wavelengths can be known in advance. Therefore, based on these data, the individual concentrations of the respective odorants may be obtained.

Referring to one sample method of deriving an individual concentration of each kind of odorant, it has been found by the present inventors, as illustrated in FIGS. 7, 8, and 9, that there exists a substantially linear function between the concentration and absorbance of each odorant. Thus, by measuring the respective absorbances of the odorants for such a plurality of wavelengths, the concentration of each of a plurality of kinds of odorants contained within a mixed system may be obtained as a mathematical solution (concentration) of the simple linear equation.

By using the above-described method, with the simple mathematical operations of obtaining respective absorbances for detection ultraviolet light having differing wavelengths, the target concentrations of the respective odorants may be reliably obtained in the individual manner, so that such subsequent operation as the concentration control of each odorant may be carried out reliably and easily.

When effecting the odorant concentration measurement, the temperature and pressure of the odorized gas may vary. Thus, it is necessary to cope with this gas temperature/pressure variation.

Hence, according to a still further method, the method further comprises:

a temperature/pressure detecting step for obtaining temperature and pressure of the odorized gas; and a step of calibrating the measured odorized gas absorbance into a calibrated absorbance under a standard condition based on the odorized gas temperature/pressure obtained by the temperature/pressure detecting step; and deriving the concentration of the odorant from the calibrated absorbance under the standard condition may be readily and easily obtained.

With the above temperature/pressure calibration, the odorant concentration under the standard condition may be readily obtained.

Preferably, the odorant comprises one or more selected from the group consisting of dimethylsulfide, tertiary butylmercaptan, tetrahydrothiophene, isopropylmercaptan, normalpropylmercaptan, ethylpropylmercaptan, and diethylsulfide.

The above-specified odorants are widely available and therefore can be used in the present invention.

Next, the detecting ultraviolet light and the correcting ultraviolet light will be more particularly described.

Preferably, the detecting ultraviolet light ranges in wavelength between 190 and 220 nm.

Ultraviolet light within the above-specified range has the required properties of high absorbability to the various odorants described hereinbefore and low absorbability to the un-odorized gas. Accordingly, by using ultraviolet light within such a wavelength range, it is possible to effect useful concentration measurement in compliance with the object of the present invention.

More particularly, it is preferred that the detecting ultraviolet light include a first specific ultraviolet light having a wavelength of 196 nm, 204 nm, or 209 nm, and a half bandwidth ranging between 0.5 and 3 nm.

Ultraviolet light within such a wavelength range as described above has the distinguished properties of high absorbability to the odorant and low absorbability to the un-odorized gas, as will be described in the embodiments. Accordingly, by using ultraviolet light within such a wavelength range, it is possible to effect useful concentration measurement in compliance with the object of the present invention.

Preferably, the correcting ultraviolet light has a wavelength ranging between 235 nm and 300 nm.

Ultraviolet light within the above-specified correcting wavelength range has the required property of low absorbability to the odorant and the hydrocarbon gas. Then, by using ultraviolet light within such a wavelength range, it is possible to effect useful concentration measurement in compliance with the object of the present invention. More particularly, it is preferred that the correcting ultraviolet light include a correction specific ultraviolet light having a wavelength of 250 nm and a half bandwidth ranging between 0.5 and 3 nm.

Ultraviolet light within such a wavelength range as above has the distinguished properties of low absorbability to the odorant and the hydrocarbon gas, as will be described in the embodiments. Accordingly, by using ultraviolet light within such a wavelength range as the correcting ultraviolet light, it is possible to effect useful concentration measurement in compliance with the object of the present invention.

Next, an apparatus for use in the invention's method of measuring odorant concentration will be described. The apparatus has the following construction, namely in an apparatus for measuring the concentration of odorant in odorized gas which is produced by adding the odorant to an un-odorized gas comprised mainly of hydrocarbon gas, the apparatus comprises an absorbance measuring mechanism for obtaining detection odorized gas absorbance which is absorbance of the odorized gas relative to a detecting ultraviolet light wavelength having high absorbability to the odorant and low absorbability to the un-odorized gas; and concentration deriving means for deriving the odorant concentration in the odorized gas by using the detection odorized gas absorbance.

With the above apparatus, the detection odorized gas absorbance is obtained by the absorbance measuring mechanism, and the concentration deriving means derives the odorant concentration from this detection odorized gas absorbance.

As described hereinbefore, when it is necessary to solve the problem of noise due to absorption by the un-odorized gas, in addition to the construction set forth above, the invention provides the apparatus with a further feature, namely The absorbance measuring mechanism is rendered capable of obtaining a second correction odorized gas absorbance which is the absorbance of the odorized gas for a correcting ultraviolet light wavelength having lower absorbability relative to the odorant and the hydrocarbon gas than the detecting ultraviolet light;

wherein, an odorant-concentration corresponding absorbance is obtained from the detection odorized gas absorbance with respect to the second correction odorized gas absorbance; and the concentration deriving means derives the odorant concentration from the odorant-concentration corresponding absorbance.

With the above odorant concentration measuring apparatus, like the method construction described hereinbefore, the absorbance measuring mechanism measures the detection odorized gas absorbance relative to the detecting ultraviolet light and the second correction odorized gas absorbance relative to the correction ultraviolet light. In this respect, the detection odorized gas absorbance relates to the odorant concentration, while the second correction odorized gas absorbance is a further datum little relating to the odorant concentration but relating to the measuring mechanism, other than the odorant and the main gas component.

Accordingly, by correcting or adjusting the detection odorized gas absorbance with reference to the second correction odorized gas absorbance as the zero point for instance, it is possible to accurately grasp the datum relating to the odorant concentration to be used for deriving the odorant concentration therefrom.

Then, according to the apparatus of the present invention, by utilizing the detection odorized gas absorbance and the second correction odorized gas absorbance obtained by the absorbance measuring mechanism, the odorant concentration corresponding absorbance relative to the second correction odorized gas absorbance is obtained from the detection odorized gas absorbance and then from this odorant concentration corresponding absorbance, the odorant concentration may be derived.

Consequently, according to the present invention, absorbance of the odorant and absorbance at the zero reference point are obtained and then the odorant concentration is derived under the proper condition, it becomes possible to effect the odorant concentration measurement in such a continuous and realtime manner. Further, the apparatus construction too may be advantageously simple because it has to deal with only the odorized gas.

Further, for measuring concentrations of a plurality of kinds of odorants, the apparatus is provided with a further construction, namely in the apparatus for measuring concentrations of a plurality of kinds of odorants added to the un-odorized gas, the apparatus comprises:

storing means for storing, as wavelengths of the detecting ultraviolet light, a plurality of wavelengths having high and differing absorbabilities relative to the odorants and low absorbability relative to the un-odorized gas;

wherein the absorbance measuring mechanism is rendered capable of individually obtaining detection odorized gas absorbances of the odorized gas for a number of the detecting ultraviolet light wavelengths greater than the number of kinds of odorants; and the concentration deriving means derives individual concentrations of the plural kinds of odorants from the individually obtained detection odorized gas absorbances of the odorized gas.

As described above, the invention's apparatus for measuring odorant concentration(s) is capable of continuous and realtime measurement of odorant concentration. Therefore, by combining this apparatus with an odorant adding system, there may be obtained an integrated system capable of effectively controlling the concentration of the added odorant(s). In this case, as the system has to deal with only the odorized gas, the system may be simple in construction, yet very useful.

Specifically, the odorant adding system of the invention comprises:

an odorant adding device for adding the odorant to the un-odorized gas; and an odorant concentration measuring apparatus as described above, the apparatus being disposed downstream of the odorant adding device; and control means for causing the odorant concentration in the odorized gas to equate with a target concentration by controlling the odorant adding device in accordance with the result of measurement by the odorant concentration measuring apparatus.

DESCRIPTION OF THE PREFERRED EMBODIMENT

Preferred embodiments of the invention will be described in detail with reference to the accompanying drawings.

Figure 1:
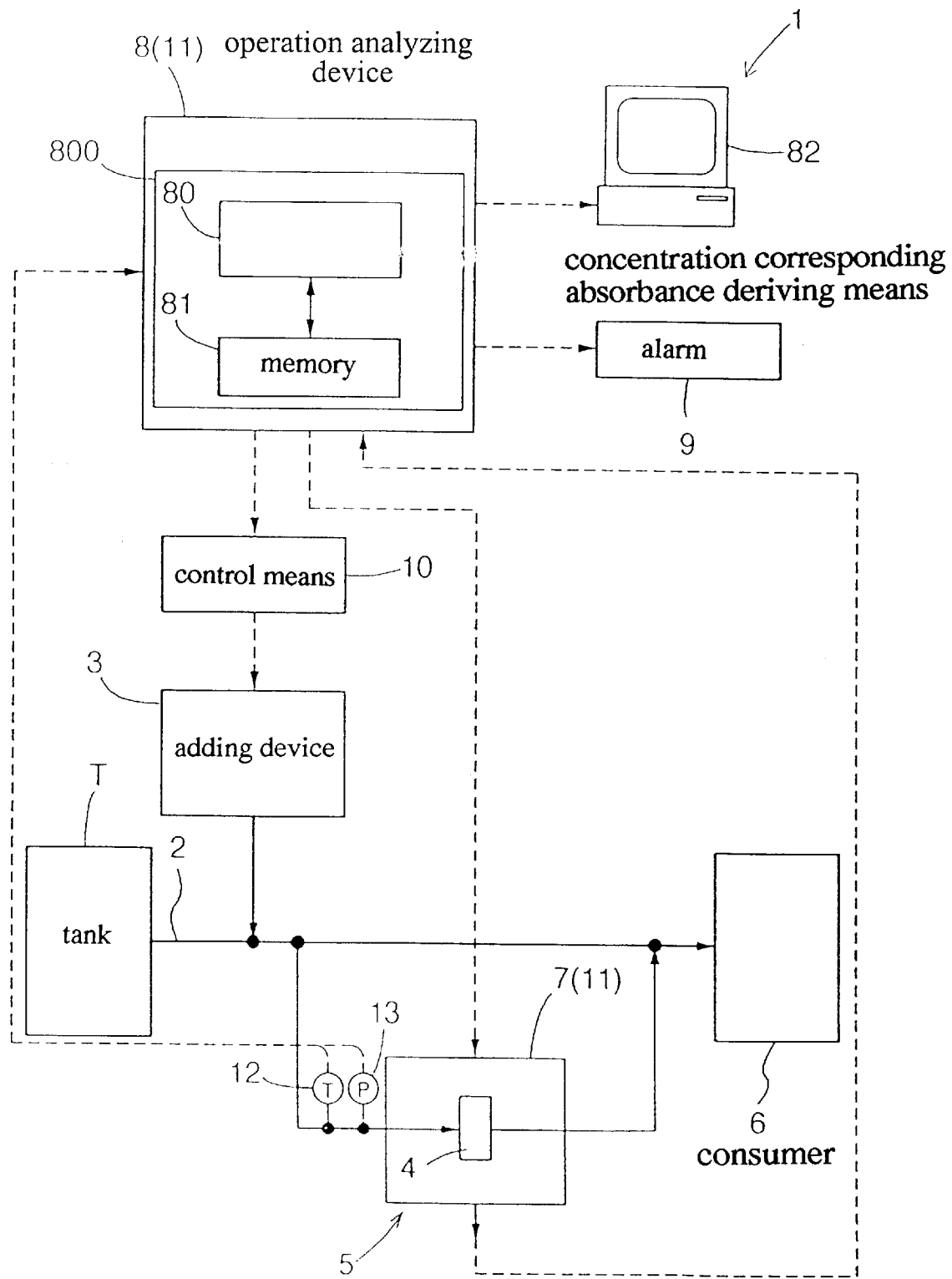
FIG. 1 shows an in-use condition of an odorant concentration measuring apparatus according to one preferred embodiment of the present invention.

FIG. 1 shows an odorant adding system in which an odorant concentration measuring apparatus 1 relating to the invention is being used.

In this diagram, there is shown a gas delivery pipe 2 connected to a tank T maintained under a high pressure of a city gas manufacturing factory for manufacturing city gas (specifically, 13A gas in the present embodiment) as an example of un-odorized gas to be supplied, in the form of odorized gas added with odorant, to consumers. The delivery pipe 2 is communicated in midway with an odorant adding device 3. Then, the odorant adding device 3 feeds odorant, whose component is known in advance, into the gas delivery pipe 2, thereby to render the un-odorized gas into the odorized gas added with the odorant. A flow cell 4 of the odorant concentration measuring apparatus 1 is incorporated within a branch portion 5 branched from the gas delivery pipe 2. Accordingly, in this apparatus of the invention, the odorized gas under high pressure is introduced into this flow cell 4 where odorant concentration measurement is effected for this introduced odorized gas.

Referring to the composition of the 13A gas, this gas is a gas mixture of a plurality of kinds of hydrocarbon gas components including, in volume, 88% of methane, 6% of ethane, 4% of propane and 2% of butane approximately.

As an odorant, there are known DMS, TBM, THT, IPM, NPM, EM, DES, and so on. In the instant embodiment, the first two of them are added together to the gas.

The gas delivery pipe 2 is maintained under a high pressure condition of about 4 to 100 kg/cm$^2$. And this pipe 2 is connected, on the downstream side thereof, with a city gas consumer site 6. Accordingly, the gas portion sampled for the odorant concentration measurement is also sent directly to the consumer site 6.

The odorant concentration measuring apparatus 1 relating to the invention includes, as main components thereof, a so-called ultraviolet absorption detector 7 and an operation analyzer device 8 comprised of a computer for controlling the operation of the ultraviolet absorption detector 7 and analyzing detection data therefrom. Also, the delivery pipe 2 incorporates therein a thermometer 12 and a pressure gauge 13. Data from detectors 12 and 13 are also sent to the analyzer device 8 to be used for subsequent operations. The apparatus 1 further includes a display/memory device 82 for effecting serial and realtime display and storage of measurement data and an alarm mechanism 9 for issuing an alarm when the measured concentration of the odorant added to the odorized gas under the high pressure exceeds either an upper or lower threshold. In constructing the entire odorant adding system, there is also provided control means 10 for appropriately controlling the amount of odorant added by the odorant adding device 3 (controlling the feeding rate of the odorant), so as to achieve the ultimate object of odorant concentration control.

Figure 2:
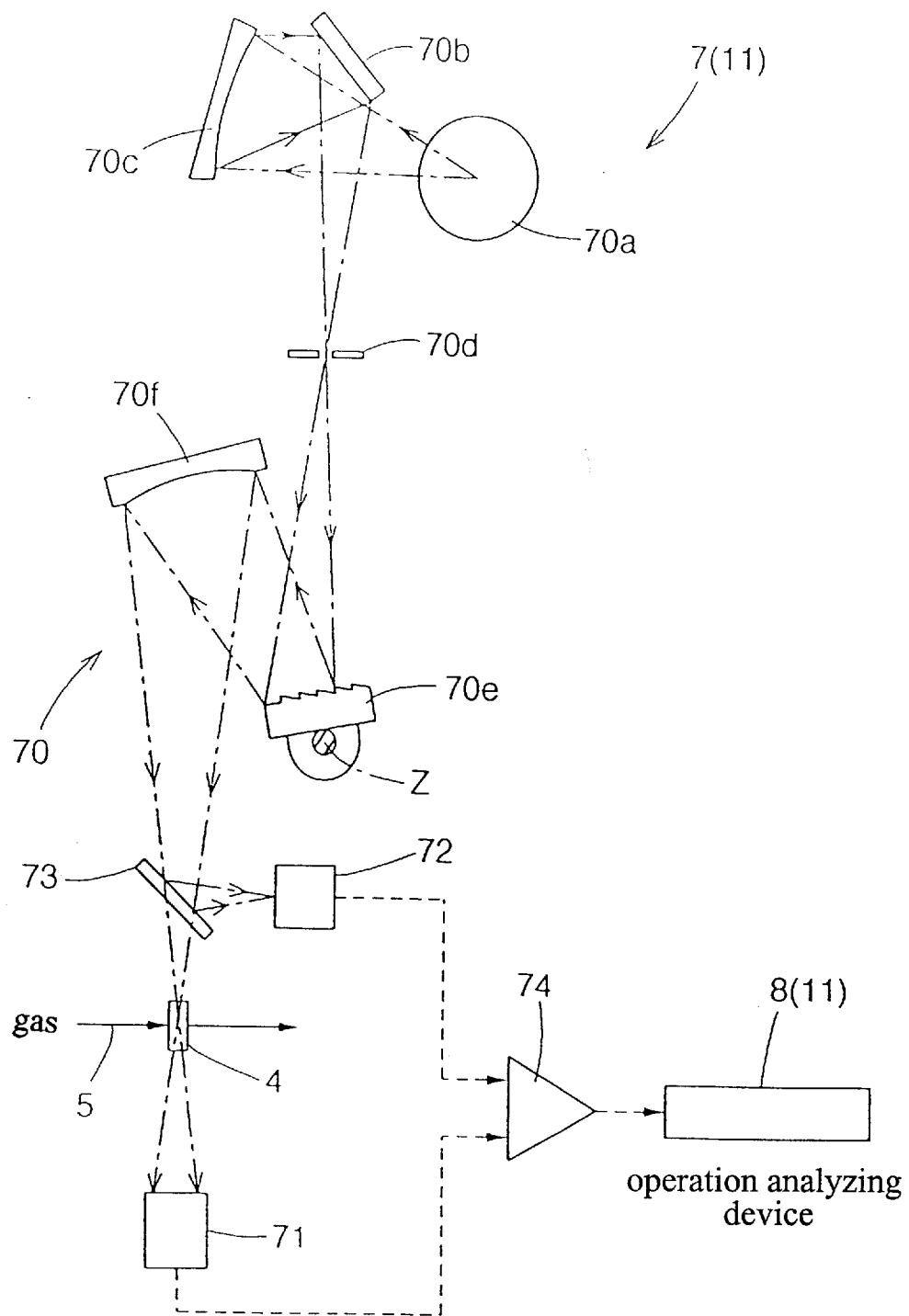
FIG. 2 shows a construction of an absorbance detector in detail.

FIG. 2 shows the construction of the ultraviolet absorption detector 7 in detail.

The ultraviolet absorption detector 7 includes the afore-described flow cell 4 as the measuring unit thereof and the detector 7 includes an optical system 70 (including a D2 lamp 70a, a plane mirror 70b, a first spherical mirror 70c, an entrance slit 70d, a diffraction grating 70e, a second spherical mirror 70f), a sampling beam detector 71 for detecting the ultraviolet light past the measuring unit, and a half mirror 73 for splitting the ultraviolet light on the upstream side of the flow cell 4 before it reaches the measuring unit and sending the splitted beam to a reference beam detector 72. The sample beam detector 71 detects intensity of the sampling beam and the reference beam detector 72 detects intensity of the reference beam and then detectors 71 and 72 transmit the detected beam intensity signals to a preamplifier 74, in which the intensity signals are amplified to be used for deriving absorbance.

In this detector 7, the diffraction grating 70e is rotatable about an axis Z extending in the depth direction of the plane of FIG. 2, so that with rotation of the grating, the wavelength of the ultraviolet light to be irradiated may be varied.

By using the above-described ultraviolet light absorption detector 7, the absorbance of the gas (the high-pressure odorized gas in this embodiment) present inside the flow cell 4 may be detected as a spectrum according to the wavelength of each ultraviolet light. In this, the detectable wavelength range is between 190 and 370 nm. Further, the flow cell 4 has an optical path length of 10 to 50 nm approximately.

The absorbance A described above is represented by a following equation:

$$A = log_{10}(I_0/I)$$

where, $I_0$ is the intensity of the reference beam and I is the intensity of the sampling beam, respectively.

The operation analyzing device 8 is constructed as an analyzing/displaying unit for obtaining the absorbances of the respective odorants based on the detection results of the ultraviolet light absorption detector 7 and deriving therefrom the concentrations of the odorants.

In this respect, the wavelengths of the data used for the analysis by the operation analyzing device 8 are of two kinds.

One kind of wavelength is that of a detecting ultraviolet light having high absorbability to the odorants and low absorbability to the un-odorized gas. Typically, its central wavelength is 196 nm, 204 nm, or 209 nm and its half bandwidth is between 0.5 and 3 nm. Ultraviolet light within these wavelength ranges are generically referred to as the detecting specific ultraviolet light in this invention. Preferably, this first kind of ultraviolet light has the wavelength ranging between 190 nm and 220 nm.

The second type of wavelength is that of a correcting ultraviolet light having low absorbability to the odorants and the hydrocarbon gas. Typically, its central wavelength is 250 nm and its half bandwidth ranges between 0.5 nm and 3 nm. Ultraviolet light within these wavelength ranges are generically referred to as the correction specific ultraviolet light in this invention. This correction specific ultraviolet light has low absorbability to both the odorants and the un-odorized gas. Preferably, this second kind of ultraviolet light has the wavelength ranging between 235 nm and 300 nm.

Then, the absorbances to the above-described two kinds of ultraviolet light are obtained by the operation analyzing device 8 from the spectrum data of the ultraviolet light absorption detector 7. In actuality, the operation analyzing device 8 is caused to store therein in advance a program adapted for obtaining the required absorbances based on an operation instruction to the ultraviolet light absorption detector 7 in conjunction with the detection data obtained according to this instruction. In this manner, with an instruction from the operation analyzing device 8, absorbance data corresponding to a desired wavelength may be obtained.

The step for obtaining the detection odorized gas absorbance which is the absorbance of the odorized gas relative to the detection ultraviolet wavelength having high absorbability to the odorant and low absorbability to the un-odorized gas (mainly, the hydrocarbon gas) will be referred to as the 'detection absorbance measuring step'. On the other hand, the step of obtaining the second correction odorized gas absorbance which is the absorbance of the odorized gas relative to the correction ultraviolet wavelength having low absorbability to the odorant and the hydrocarbon gas will be referred to as the 'second correction absorbance measuring step'.

Now, from these detection odorized gas absorbance and second correction odorized gas absorbance obtained in the manner described above, the target absorbance truly dependent on the odorant concentration (the odorant concentration corresponding absorbance) is obtained. For this purpose, the operation analyzing device 8 includes a concentration corresponding absorbance deriving means 80, which determines a difference value obtained by subtracting the second correction odorized gas absorbance from the detection odorized gas absorbance as the odorant concentration corresponding absorbance. In this fashion, it is possible to obtain normalized data with respect to the second correction odorized gas absorbance as the zero point (a kind of reference point).

Accordingly, with the apparatus 1 of the present invention, the measurement of the absorbance relative to the detection ultraviolet wavelength and the measurement of the absorbance relative to the correction ultraviolet wavelength are effected on substantially identical odorized gas. As a result, reliable data, i.e. odorant concentration may be obtained.

The odorant concentration corresponding absorbance is obtained for each of the three kinds of detection ultraviolet wavelengths described hereinbefore.

This odorant concentration measuring apparatus 1 is capable also of detecting or monitoring the temperature and pressure of the odorized gas under the condition for the odorant concentration measurement. Hence, the above-described absorbances (i.e. each of the odorant concentration corresponding absorbances or the absorbances without the zero-point adjustment) are adjusted or calibrated, in accordance with the detected temperature and pressure of the odorized gas, into temperature/pressure calibrated absorbances under the standard condition (absolute pressure: 30kgf/cm$^2$, temperature 20° C.).

This calibration is done according to an expression as follows:

temperature/pressure calibrating expression for absorbance (standard: absolute pressure of 30 kgf/cm$^2$)

$$A = \frac{ai - K\lambda}{(Pi + 1.033)} \cdot 30 \cdot \frac{(273.15 + ti) \rightarrow}{(273.15 + 20) \rightarrow}$$

where;

A: calibrated absorbance corresponding to standard odorant concentration at absolute pressure of 30 kgf/cm$^2$ ai: odorant concentration corresponding absorbance after zero point adjustment according to the invention's method Pi: gauge pressure (kgf/cm$^2$) of sampling gas at the time of measurement ti: temperature (° C.) of sampling gas at the time of measurement k$\lambda$: absorbance calibrating coefficient '0' for 196 nm wavelength '−0.001' for 204 nm wavelength '0' for 209 nm wavelength '0' for 250 nm wavelength As a result, with this apparatus 1, it is always possible to obtain odorant concentration corresponding to the standard condition.

Figure 7:
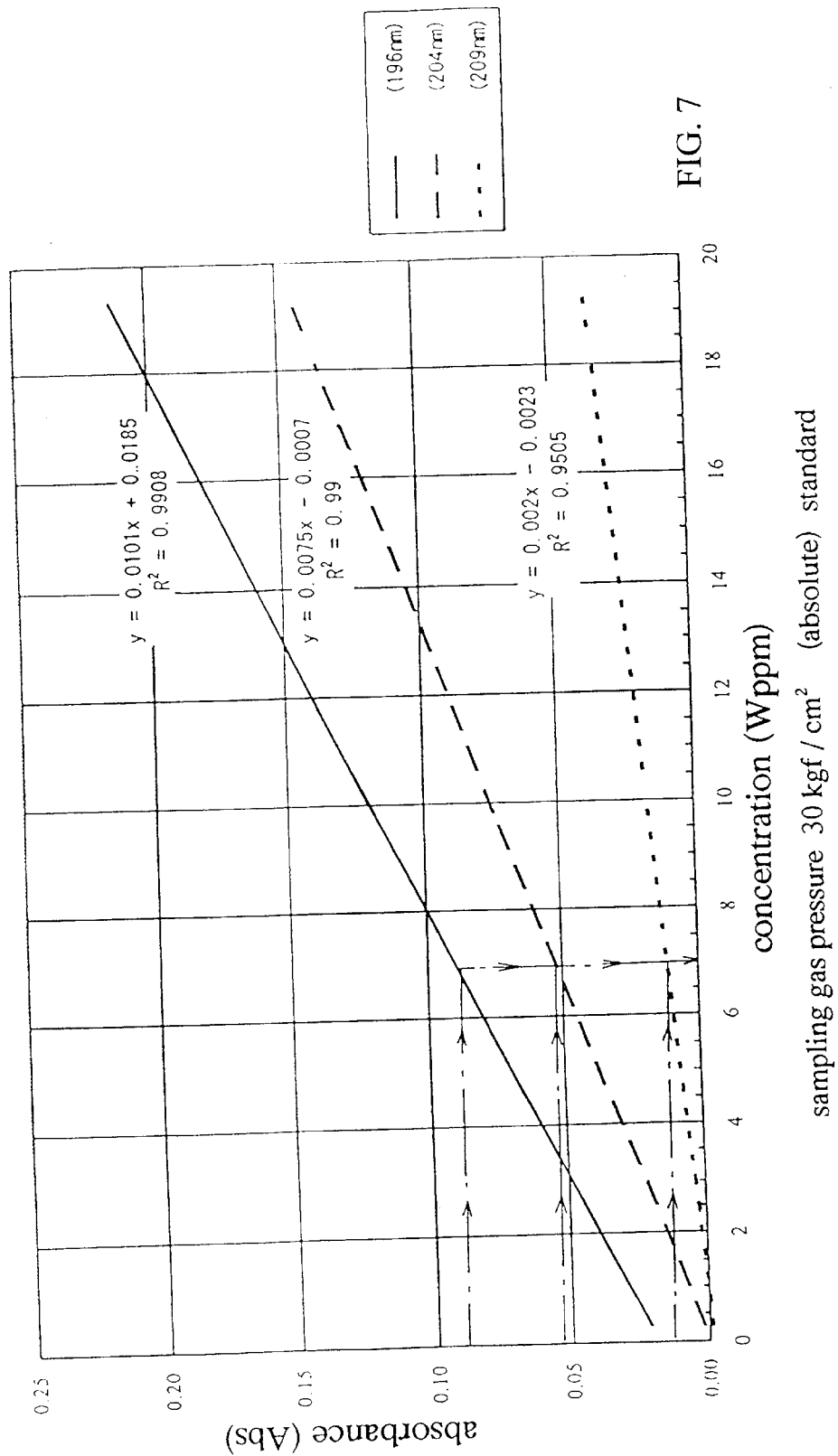
FIG. 7 is a graph showing relation between the concentration and the absorbance of DMS.
Figure 8:
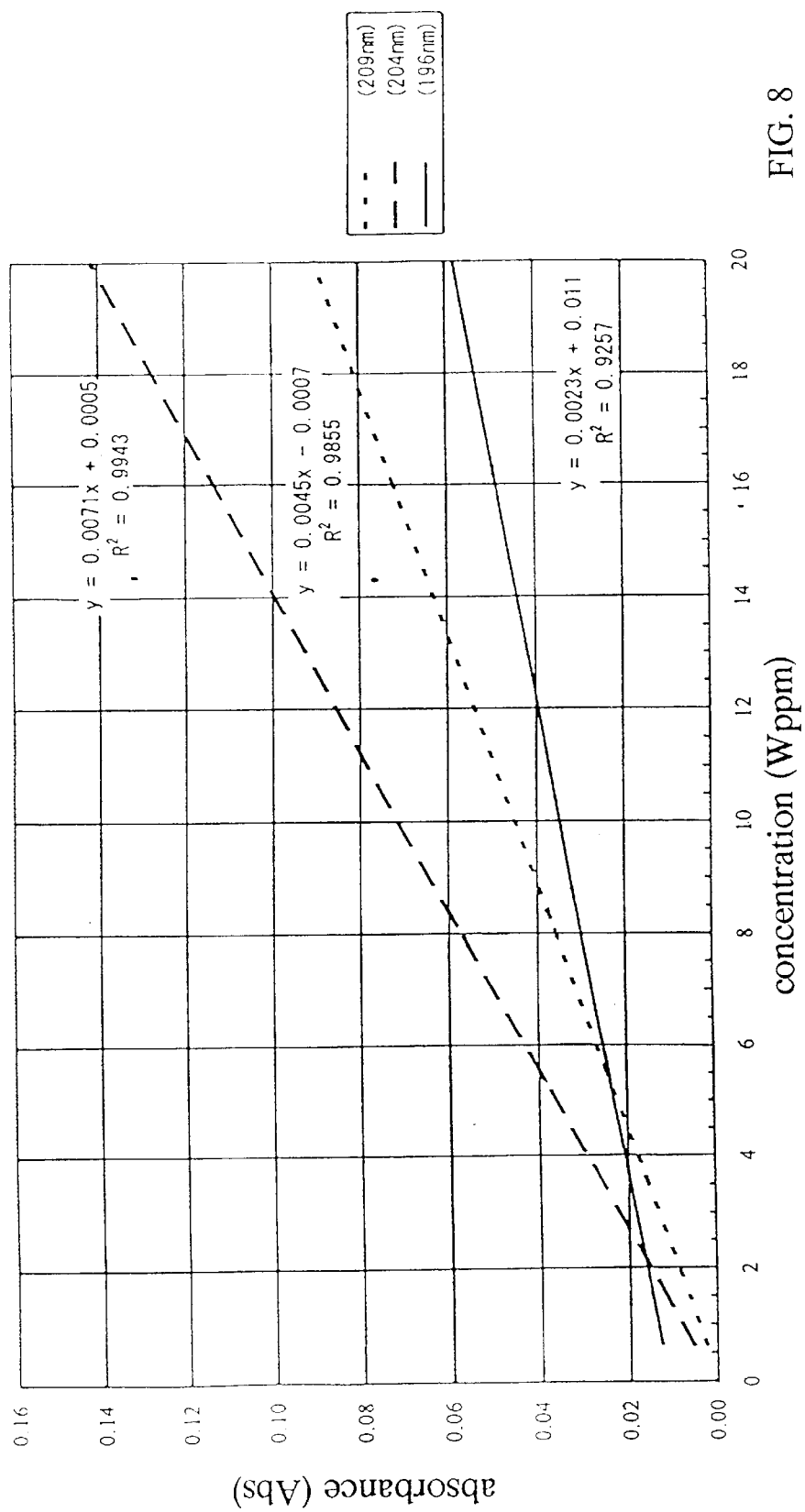
FIG. 8 is a graph showing relation between the concentration and the absorbance of TBM.
Figure 9:
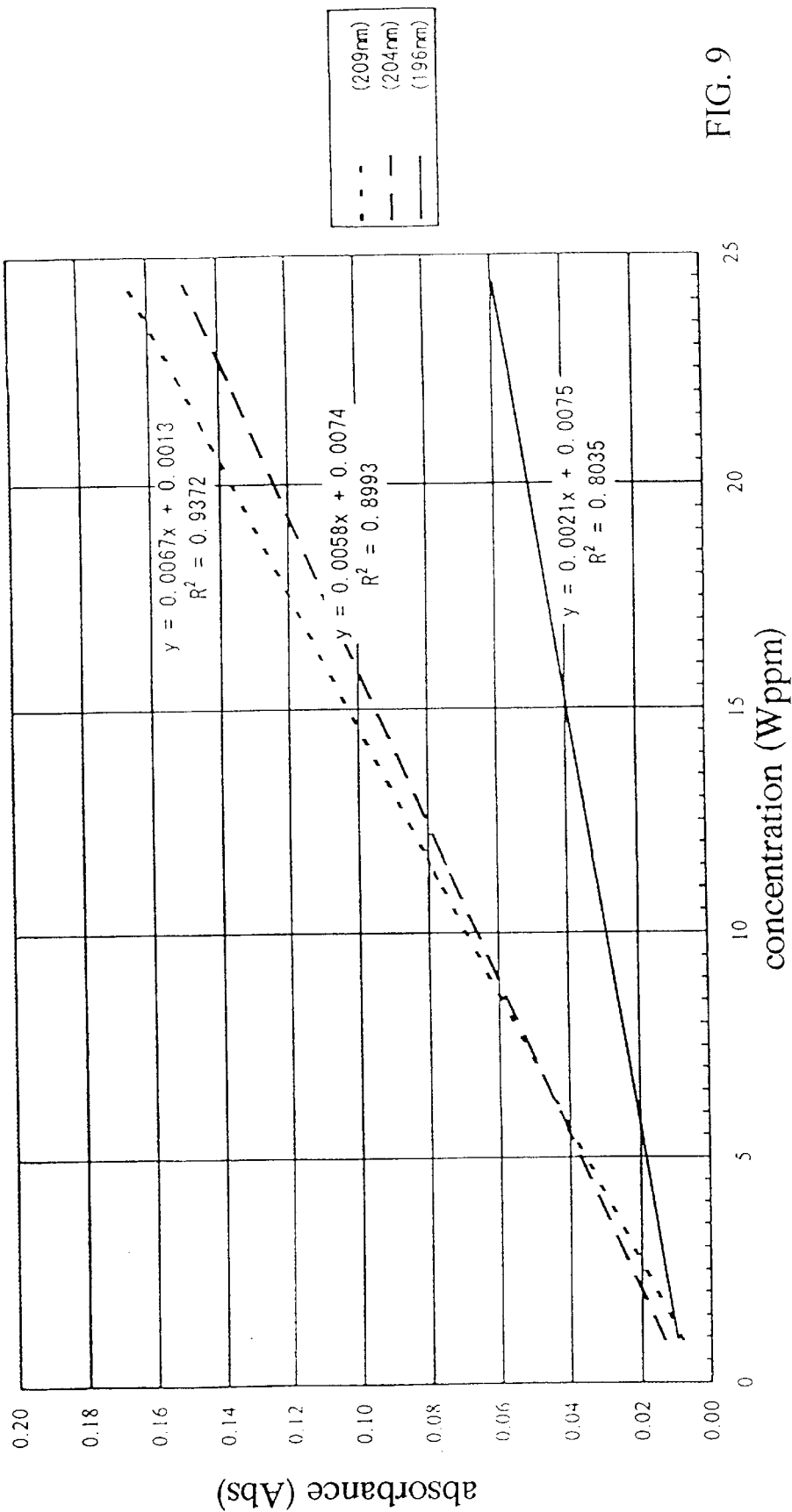
FIG. 9 is a graph showing relation between the concentration and the absorbance of THT.

Next, there will be described a method of deriving the odorant concentration from the odorant concentration corresponding absorbance obtained in the manner described above. For this operation, there are employed relational indices (essentially, linear functional expressions), as shown in FIGS. 7, 8, and 9, between each odorant concentration and an odorant concentration corresponding absorbance. The operation analyzing device 8 stores, in its memory 81, such relational indices, so that the concentration of each odorant may be obtained with specification of the absorbance as denoted with broken-line arrows in FIG. 7.

When two kinds of odorants (i.e. DMS and TBM) are used in the mixed state as is the case with the instant embodiment, the concentration of each odorant may be obtained by solving a following expression:

$$\begin{pmatrix} A_{(196\ nm)} \\ A_{(204\ nm)} \end{pmatrix} = \begin{pmatrix} a_{(196\ nm.\ DMS)} & a_{(196\ nm.\ TBM)} \\ a_{(204\ nm.\ DMS)} & a_{(204\ nm.\ TBM)} \end{pmatrix} \begin{pmatrix} C_{(DMS)} \\ C_{(TBM)} \end{pmatrix} + \begin{pmatrix} b_{(196\ nm)} \\ b_{(204\ nm)} \end{pmatrix}$$

where, A denotes absorbance measured for a specific wavelength, and subscripts denote the kinds of wavelength and odorant. Further, C denotes the concentration of each odorant, and the subscript denotes the kind of odorant.

Further, the coefficients 'a', 'b' are as follows:

$a(196\ nm, DMS) = 0.009557$ $a(196\ nm, TBM) = 0.002402$ $b(196\ nm) = 0.01788$ $a(204\ nm, DMS) = 0.006936$ $a(204\ nm, TBM) = 0.007171$ $b(204\ nm) = 0.01343$

These values are determined from the relational indices shown in FIGS. 7, 8 and 9.

The combination of wavelengths may be any two of the three kinds described hereinbefore.

As described above, the odorant concentration measuring apparatus 1 of the invention includes the absorbance measuring mechanism 11 (including specifically the ultraviolet light absorption detector 7 and the means for obtaining the odorant concentration corresponding absorbance for each detection ultraviolet light wavelength based on the measurement result of the detector 7) capable of measuring the detection odorized gas absorbance which is the absorbance of the odorized gas relative to the detecting ultraviolet light having the detection ultraviolet wavelength having high absorbability to the odorant and low absorbability to the un-odorized gas, and the second correction odorized gas absorbance which is the absorbance of the odorized gas relative to the correcting ultraviolet light having the correction ultraviolet wavelength having low absorbability to the odorant and the hydrocarbon gas, and the concentration corresponding absorbance deriving means 80 for deriving, from the detection odorized gas absorbance, the odorant concentration corresponding absorbance with respect to the second correction odorized gas absorbance as the reference point, so that the odorant concentration is obtained based on the odorant concentration corresponding absorbance derived by the concentration corresponding absorbance deriving means 80. Further, the means for deriving the odorant concentration from the absorbance will be referred to as 'concentration deriving means 800'.

Next, the entire operation of the apparatus 1 will be described in connection with the invention's method of measuring odorant concentration.

When the apparatus 1 is under operation, odorized gas is introduced into the flow cell 4 and the ultraviolet absorption detector 7 is operated continuously according to an instruction from the operation analyzing device 8, so as to detect the detection odorized gas absorbances (2 kinds selected from the above-described 3 kinds and when the above expression is used, these correspond specifically to the specific ultraviolet light having the central wavelengths of 196 nm and 204 nm) and the second correction odorized gas absorbance (1 kind). Next, from each obtained detection odorized gas absorbance, the second correction gas absorbance is subtracted, and using the temperature/pressure data simultaneously obtained, the temperature/pressure calibration is effected, whereby the odorant concentration corresponding absorbance is obtained. Then, from this odorant concentration corresponding absorbance, the concentration of each odorant is derived with reference to the corresponding pre-stored relational index as shown in FIG. 7, 8, or 9.

In the above-described manners, the concentrations of odorants may be obtained.

Experiments were conducted in accordance with the above-described method, for 4 runs on a mixture system of DMS (2 ppm) and TBM (0.3 ppm) under a gas gauge pressure ranging from 15 to 40 kgf/cm$^2$ (increased stepwise by 5 kgf/cm$^2$ each). Hence, the measurements were conducted for total of 24 runs. Then, substantially no differences were found between the measurements according to the method of the invention and those according to a FPD gas chromatograph with respect to the average values DMS (2.01 ppm), TBM (0.31 ppm)). Odorant concentration measurement of such high precision has been made possible for the first time by the present invention.

The present inventors conducted an experiment to verify the reliability of the odorant concentration measuring method and apparatus 1 of the present invention. Next, this experiment will be described.

1. Ultraviolet Light Absorption Spectra of Odorants

Figure 3:
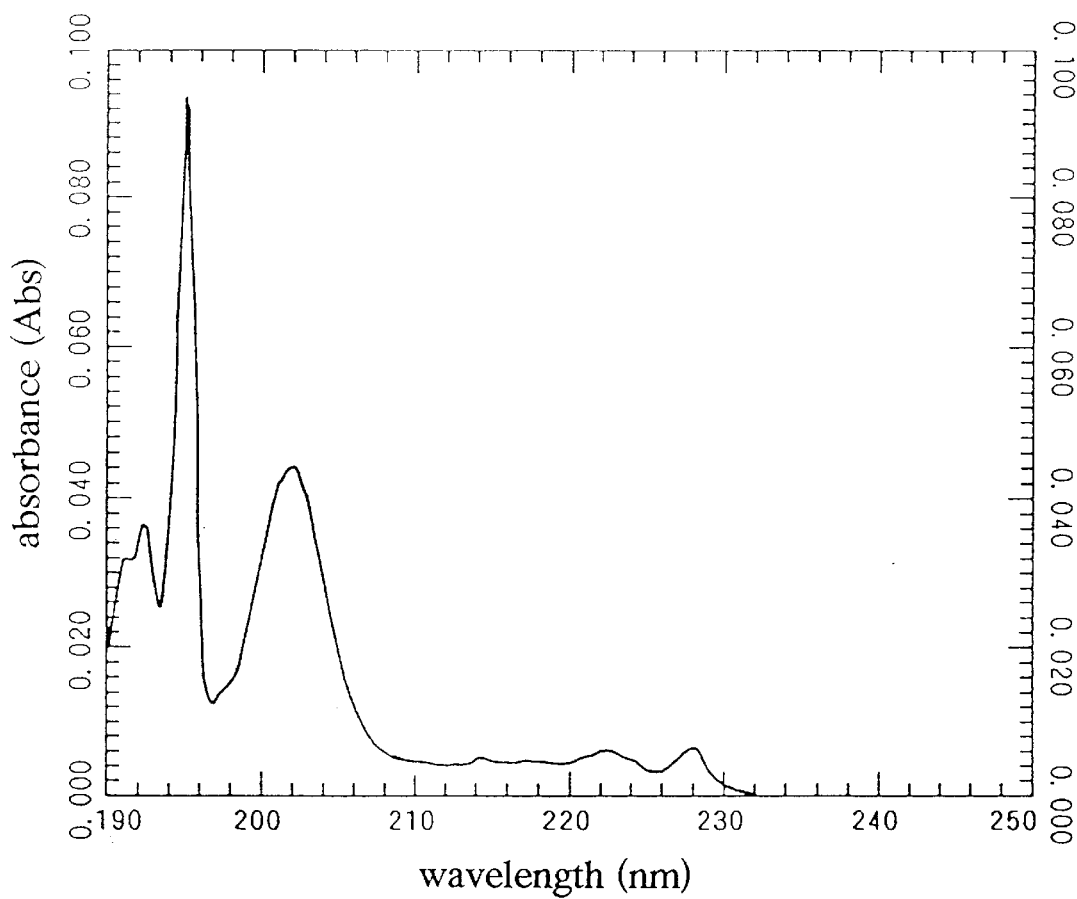
FIG. 3 is a graph showing an absorption spectrum of odorized gas added with DMS.
Figure 4:
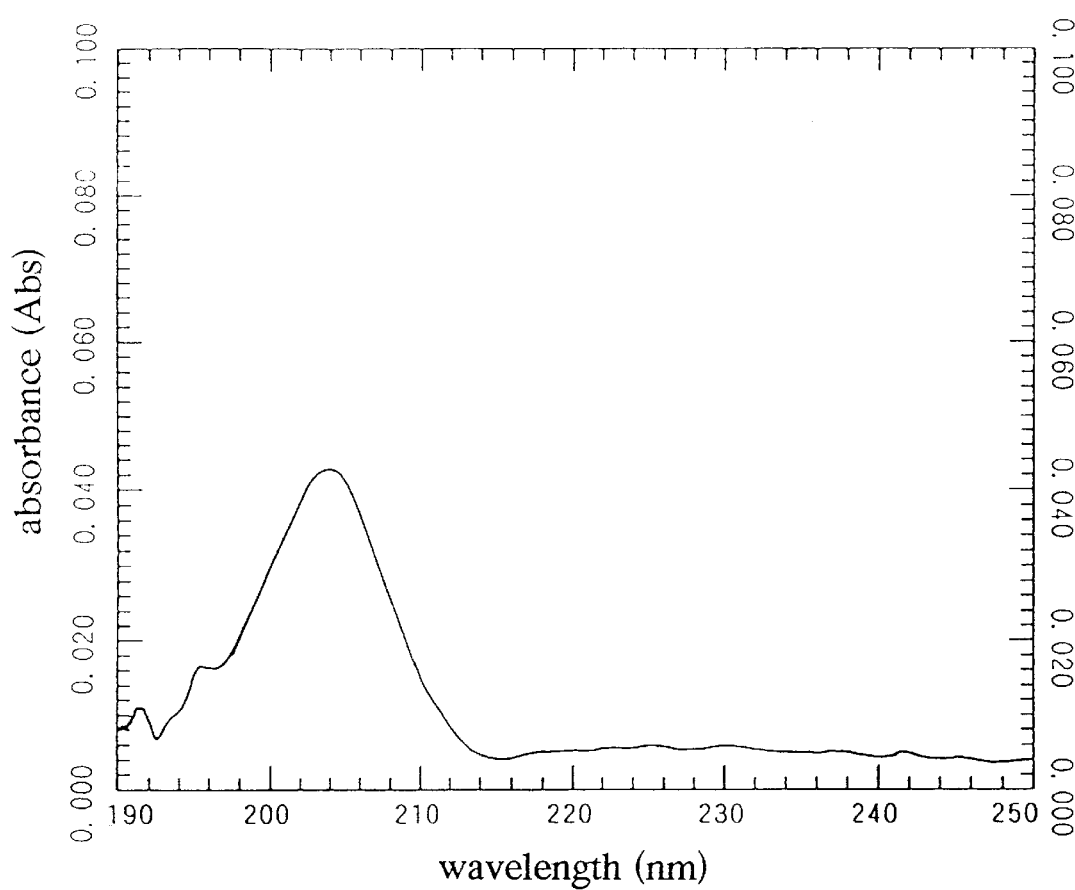
FIG. 4 is an absorption spectrum of odorized gas added with TBM.
Figure 5:
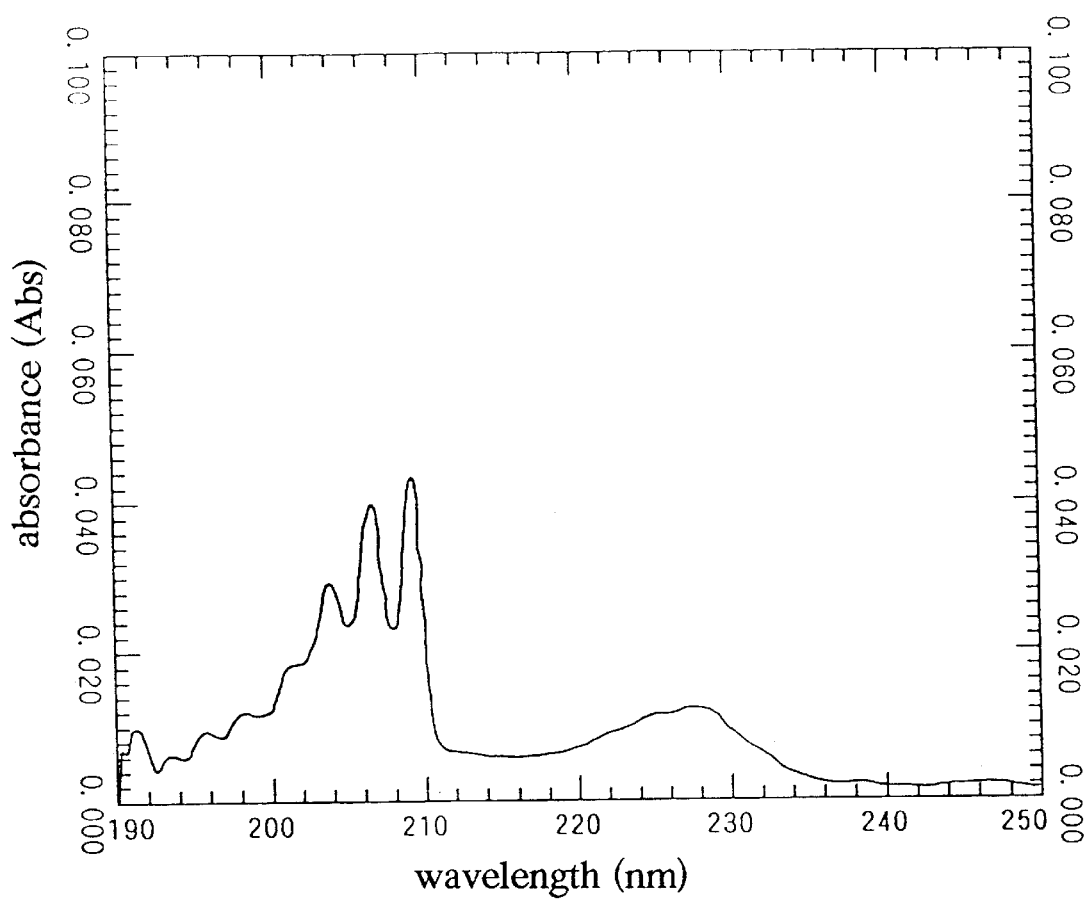
FIG. 5 is an absorption spectrum of odorized gas added with THT.
Figure 6:
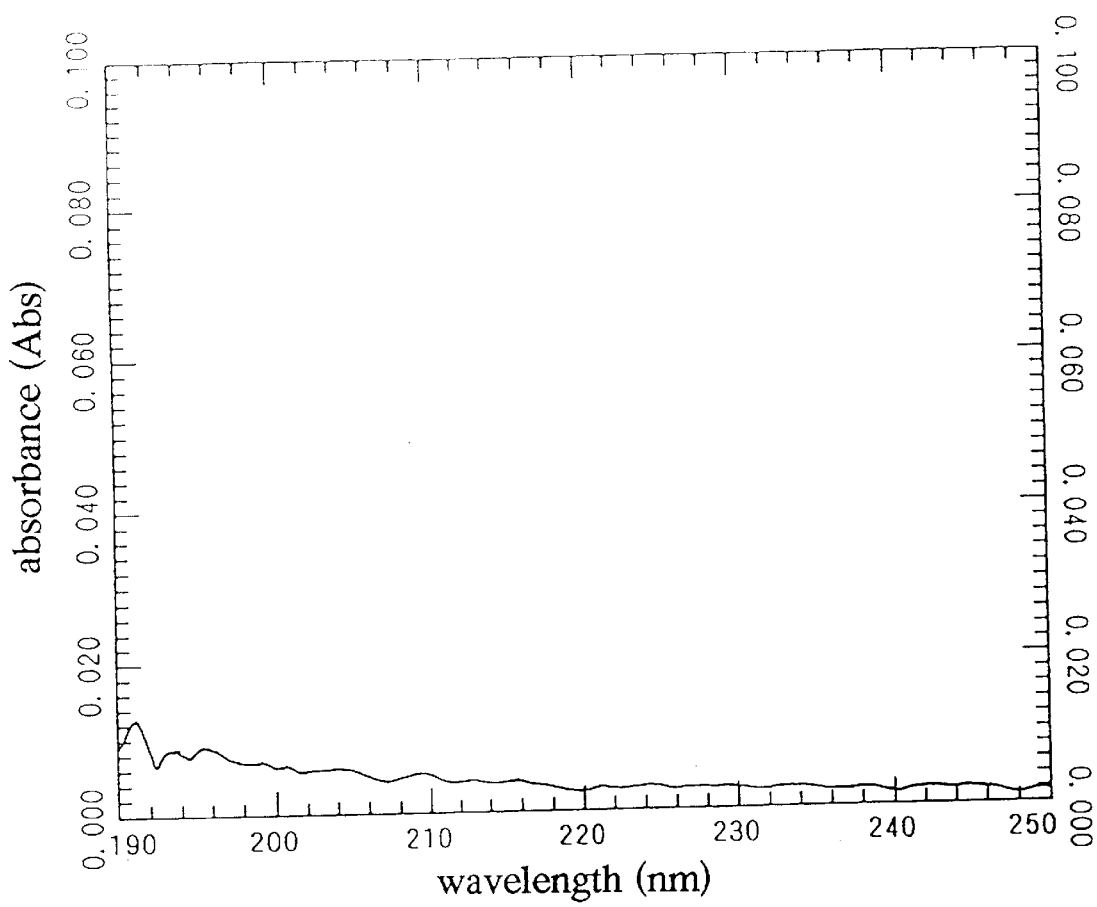
FIG. 6 is an absorption spectrum of 13A gas as an un-odorized gas.

An absorption spectrum of each of the afore-mentioned odorants, DMS, TBM and THT was obtained. FIGS. 3, 4, and 5 show these absorption spectra, respectively. Also, FIG. 6 shows the absorption spectrum of the 13A gas which is employed as the base, i.e. un-odorized gas in the present embodiment. The ultraviolet light used had the wavelength range of 190 to 250 nm. As may be apparent from these graphs, ultraviolet light of certain wavelengths have low absorbability to both the 13A gas and the odorant, while others have low absorbability to the former and high absorbability to the latter.

2. Relationship Between Absorbance and Concentration of Odorant 2.1: Concentration Dependency of DMS Absorbance The result of this experiment is shown in FIG. 7. As shown, for all the detection specific ultraviolet light having the wavelengths of 196 nm, 204 nm and 209 nm respectively, the absorbance increases in proportion to the DMS concentration. In this manner, there exists a good proportional relationship between the absorbance and the concentration. In the same graph, regression lines represented by equations are relational regression lines between the absorbance and the odorant concentration (relate to DMS alone) corresponding respectively to the three kinds of detecting ultraviolet light.

Accordingly, when DMS alone is added as odorant, by obtaining the absorbances for he above-described detection specific ultraviolet light wavelengths, the concentration of this kind of odorant may be obtained.

2.2: Concentration Dependency of TBM Absorbance

The result of this experiment is shown in FIG. 8. As shown, for all the detection specific ultraviolet light having the wavelengths of 196 nm, 204 nm, and 209 nm respectively, the absorbance increases in proportion to the TBM concentration. In this manner, there exists a good proportional relationship between the absorbance and the concentration. In the same graph, regression lines represented by equations are relational regression lines between the absorbance and the odorant concentration (relate to TBM alone) corresponding respectively to the three kinds of detection ultraviolet light wavelengths.

Accordingly, when TBM alone is added as odorant, by obtaining the absorbances for the above-described detection specific ultraviolet light wavelengths, the concentration of this kind of odorant may be obtained.

2.3: Concentration Dependency of THT Absorbance

The result of this experiment is shown in FIG. 9. As shown, for all the detection specific ultraviolet light having the wavelengths of 196 nm, 204 nm, and 209 nm respectively, the absorbance increases in proportion to the THT concentration. In this manner, there exists a good proportional relationship between the absorbance and the concentration. In the same graph, regression lines represented by equations are relational regression lines between the absorbance and the odorant concentration (relate to THT alone) corresponding respectively to the three kinds of detection ultraviolet light wavelengths.

Accordingly, when THT alone is added as odorant, by obtaining the absorbances for the above-described detection specific ultraviolet wavelengths, the concentration of this kind of odorant may be obtained.

Some other embodiments of the present invention will be described next.

In the foregoing embodiment, DMS and TBM are mixedly used as the main odorants. But, the present invention may be applied also in case THT or the like is used.

Further, in the foregoing embodiment, the un-odorized gas comprises the city gas (13A). Yet, the invention may be applied to any gas containing hydrocarbon.

Then, if hydrocarbon gas having a carbon number of 4 or less is used as the un-odorized gas and one or more kinds selected from the group consisting of DMS, TBM, THT and so on are used as the odorants, it is preferred that the detecting ultraviolet light has a wavelength ranging between 190 nm and 220 nm. Ultraviolet light within such a wavelength range has low absorbability to the hydrocarbon gas and high absorbability to the odorants, so that the measurements may be effected accurately.

Further, in the foregoing embodiment, the correcting ultraviolet light has the central wavelength of 250 nm and the half bandwidth of 0.5 to 3 nm. Instead, the correcting ultraviolet light may have a different wavelength ranging between 235 nm and 300 nm.

In the foregoing embodiment, two kinds of odorants are added as the odorants. However, even when only one kind of odorant or more than three kinds of odorants are added, the concentration of each odorant may be obtained using the same mathematical expression by increasing the number of ultraviolet light of differing wavelengths in accordance with the number of the odorant(s).

In the above, when only one kind of odorant is used and the concentration of this odorant is to be obtained based on absorbances thereof relative to ultraviolet light of a plurality of wavelengths, it is conceivable to obtain e.g. an average of the sum of the concentrations obtained from the respective wavelengths, whereby the odorant concentration with greater precision may be obtained. For instance, supposing a concentration of DMS is to be obtained, measured concentration values will be obtained respectively from the three index lines in FIG. 7 and then an average of these values will be taken. Then, this average value will show the DMS concentration with greater accuracy.

On the other hand, if absorbances relative to ultraviolet light of differing wavelengths are to be obtained for measurement of concentrations of a plurality of kinds of odorants, the concentration of each odorant may be obtained by using the same mathematical operations described above. In this case, the only requirement is that the number of ultraviolet light having differing wavelengths be greater than the number of kinds of odorants.

Moreover, it is also possible to take plural kinds of odorants as a single group. That is, in case e.g. two kinds of odorant are mixedly used, the absorbance property of this mixture will be determined in advance. Then, from this, concentration of this odorant mixture may be measured.

In deriving the odorant concentration from the absorbance of the odorized gas, alternatively from the relational graphs shown in FIGS. 7, 8, and 9, relational tables or approximate expressions such as linear approximate expressions may be employed. What is essential here is that the odorant concentration be obtained with reference to some relational index which is known in advance.

The odorant concentration measuring apparatus of the invention may be installed at any site, instead of the actual gas delivery site under high pressure.

Conventionally, the measurement of odorant concentration has been effected with sample gas being maintained under a near-atmospheric pressure condition, as described hereinbefore. The method and apparatus of the present invention may be used under such pressure-reduced condition as well. However, the present invention may be embodied more advantageously when the odorized gas is placed under a high pressure because the presence of greater amount of odorant(s) facilitates the measurement, in contrast to the conventional art. For this reason, the method, apparatus and system according to the present invention are advantageous in that they may be readily applied to the actual existing situation. In addition to this advantage, the present invention provides the further advantage of the possibility of more accurate continuous measurement, recording and control of odorant concentration.

In the foregoing embodiment, for effecting the so-called zero-point adjustment, this is done by obtaining the absorbance of the odorized gas relative to the correcting ultraviolet light. Needless to say, this adjustment may be made based on the un-odorized gas, rather than on the odorized gas. In this case, the process will comprise a following construction, in which the detecting ultraviolet light is utilized for the adjustment like the measuring step. Namely, the method further comprises a first correction absorbance measuring step of obtaining a first correction un-odorized gas absorbance which is absorbance of the un-odorized gas relative to the detecting ultraviolet light. Then, the odorant-concentration corresponding absorbance is obtained from the detection odorized gas absorbance with respect to the first correction un-odorized gas absorbance. In the subsequent concentration deriving step, the odorant concentration is derived from this odorant-concentration corresponding absorbance.

In the above description, the odorized gas absorbance and the first correction un-odorized gas absorbance are obtained and further the odorant absorbance is obtained as a difference therebetween, from which the difference the odorant concentration is derived. In this respect, it should be noted that the detecting ultraviolet light used in the present invention basically has low or negligible absorbability relative to the un-odorized gas, so that the first correction un-odorized gas absorbance may be defined as '0' (zero). Accordingly, in this case, the method construction may be modified such that the odorant concentration is obtained directly from the odorized gas absorbance without effecting the subtracting operation described above.

With this, the apparatus or system construction too may be simplified and its costs may be reduced advantageously.

Moreover, in some cases, direct measurements of the correction absorbances (the first and second) may be not needed at all. That is, the properties of the un-odorized gas are strictly controlled when the gas is manufactured, so that it may be reasonably assumed that its properties are relatively stable. Therefore, it is conceivable to store in advance the standard absorbance of such gas in a memory, so that this stored absorbance is read from the memory when needed and this is subtracted from the actually measured absorbance of the odorized gas.

What is claimed is:

1. A method of measuring a concentration of odorant in odorized gas which is produced by adding the odorant to un-odorized gas comprised mainly of hydrocarbon gas, which comprises:

a detection absorbance measuring step for obtaining, detection odorized gas absorbance which is absorbance of the odorized gas relative to a detecting ultraviolet light having high absorbability to the odorant and low absorbability to the un-odorized gas; and a concentration deriving step for deriving the odorant concentration in the odorized gas by using the detection odorized gas absorbance;

wherein said detecting ultraviolet light includes a first specific ultraviolet light having a wavelength selected from the group consisting of 196 nm, 204 nm, and 209 nm and a half bandwidth of between 0.5 to 3 nm.

2. The method according to claim 1, further comprising:

a first correction absorbance measuring step of obtaining a first correction un-odorized gas absorbance which is absorbance of the un-odorized gas relative to said detection ultraviolet light;

wherein, an odorant-concentration corresponding absorbance is obtained from the detection odorized gas absorbance with respect to the first correction un-odorized gas absorbance; and in the concentration deriving step, the odorant concentration is derived from the odorant-concentration corresponding absorbance.

3. The method according to claim 1, further comprising:

a second correction absorbance measuring step of obtaining a second correction odorized gas absorbance which is the absorbance of the odorized gas for a correcting ultraviolet light having lower absorbability relative to the odorant and hydrocarbon gas than said detecting ultraviolet light;

wherein, an odorant-concentration corresponding absorbance is obtained from the detection odorized gas absorbance with respect to the second correction odorized gas absorbance; and wherein in the concentration deriving step, the odorant concentration is derived from the odorant-concentration corresponding absorbance.

4. The method according of claim 1, in which a plurality of kinds of odorants are added to the un-odorized gas, the method comprising the steps of:

selecting in advance, as wavelengths of the detection ultraviolet ray, a plurality of wavelengths having high and differing absorbabilities relative to the odorants and low absorbability relative to the un-odorized gas;

individually obtaining detection odorized gas absorbances of the odorized gas for a number of the detection ultraviolet wavelengths greater than the number of kinds of odorants; and deriving individual concentrations of the plural kinds of odorants from the individually obtained detection odorized gas absorbances of the odorized gas.

5. The method according to claim 1, further comprising:

a temperature/pressure detecting step for obtaining temperature and pressure of the odorized gas;

a step of calibrating the measured odorized gas absorbance into a calibrated absorbance under a standard condition based on the odorized gas temperature and pressure obtained by the temperature/pressure detecting step; and deriving concentration of the odorant from the calibrated absorbance under the standard condition.

6. The method according of claim 1, wherein the odorant comprises at least one odorant selected from the group consisting of dimethylsulfide, tertiary butylmercaptan, tetrahydrothiophene, isopropylmercaptan, n-propyhnercaptan, ethylpropylmercaptan, and diethylsulfide.

7. The method according to claim 3, wherein the correcting ultraviolet light has a wavelength ranging between 235 nm and 300 nm.

8. The method claim 3, wherein the correcting ultraviolet light includes a correction specific ultraviolet light having a wavelength of 250 nm and a half bandwidth ranging between 0.5 and 3 nm.

9. An apparatus for measuring a concentration of odorant in odorized gas which is produced by adding the odorant to un-odorized gas comprised mainly of hydrocarbon gas, the apparatus comprising:

an absorbance measuring mechanism for obtaining a detection odorized gas absorbance which is absorbance of the odorized gas relative to a detecting ultraviolet light having high absorbability to the odorant and low absorbability to the un-odorized gas; and a concentration deriving means for deriving the odorant concentration in the odorized gas by using the detection odorized gas absorbance;

wherein said detecting ultraviolet light includes a first specific ultraviolet light having a wavelength selected from the group consisting of 196 nm, 204 nm, and 209 nm and a half bandwidth of between 0.5 to 3 nm.

10. The apparatus according to claim 9, wherein the absorbance measuring mechanism is rendered capable of obtaining a second correction odorized gas absorbance which is absorbance of the odorized gas for a correcting ultraviolet light having lower absorbability relative to the odorant and hydrocarbon gas than said detecting ultraviolet light;

an odorant-concentration corresponding absorbance is obtained from the detection odorized gas absorbance with respect to the second correction odorized gas absorbance; and the concentration deriving means derives the odorant concentration from the odorant-concentration corresponding absorbance.

11. The apparatus according to claim 9, in which the apparatus is adapted for measuring concentrations of a plurality of kinds of odorants added to the un-odorized gas, the apparatus comprising:

storing means for storing, as wavelengths of the detecting ultraviolet light, a plurality of wavelengths having high and differing absorbabilities relative to the odorants and low absorbability relative to the un-odorized gas;

wherein the absorbance measuring mechanism is rendered capable of individually obtaining detection odorized gas absorbances of the odorized gas for a number of the detecting ultraviolet wavelengths greater than the number of kinds of odorants; and the concentration deriving means derives individual concentrations of the plural kinds of odorants from the individually obtained detection odorized gas absorbances of the odorized gas.

12. An odorant adding system comprising:

an odorant adding device for adding the odorant to the un-odorized gas;

the odorant concentration measuring apparatus according to claim 9, the apparatus being disposed downstream of the odorant adding device; and control means for causing the odorant concentration in the odorized gas to equate with a target concentration by controlling the odorant adding device in accordance with the result of measurement by the odorant concentration measuring apparatus.

13. An odorant adding system comprising:

an odorant adding device for adding the odorant to the un-odorized gas;

the odorant concentration measuring apparatus according to claim 10, the apparatus being disposed downstream of the odorant adding device; and control means for causing the odorant concentration in the odorized gas to equate with a target concentration by controlling the odorant adding device in accordance with the result of measurement by the odorant concentration measuring apparatus.

14. An odorant adding system comprising:

an odorant adding device for adding the odorant to the un-odorized gas;

the odorant concentration measuring apparatus according to claim 11, the apparatus being disposed downstream of the odorant adding device; and control means for causing the odorant concentration in the odorized gas to equate with a target concentration by controlling the odorant adding device in accordance with the result of measurement by the odorant concentration measuring apparatus.

* * * * *

UNITED STATES PATENT AND TRADEMARK OFFICE
CERTIFICATE OF CORRECTION

PATENT NO. : 5, 844, 124
DATED : Dec. 1, 1998
INVENTOR(S) : Shimokawatoko, et al.

It is certified that error appears in the above-identified patent and that said Letters Patent is hereby corrected as shown below:

In column 12, line 41, change "he" to - - the - -.

Signed and Sealed this

Fourth Day of July, 2000

Attest:

Q. TODD DICKINSON

Attesting Officer

Director of Patents and Trademarks